United States Patent [19]

Zoeller et al.

[11] Patent Number: 4,965,399

[45] Date of Patent: Oct. 23, 1990

[54] 1,5-DIARYL-3-PENTANOL COMPOUNDS AND PROCESSES FOR THE PREPARATION THEREOF

[75] Inventors: Joseph R. Zoeller, Kingsport; William W. Blount, Surgoinsville, both of Tenn.

[73] Assignee: Eastman Kodak Company, Rochester, N.Y.

[21] Appl. No.: 233,789

[22] Filed: Aug. 19, 1988

[51] Int. Cl.$^5$ .............................................. C07C 69/76
[52] U.S. Cl. ..................................... 560/64; 562/473; 568/644; 564/171
[58] Field of Search .......................... 560/64; 562/473; 568/644; 564/171

[56] References Cited

U.S. PATENT DOCUMENTS 4,778,925 10/1988 Grill ..................................... 562/473

FOREIGN PATENT DOCUMENTS 1442133 7/1976 United Kingdom .

OTHER PUBLICATIONS

C.A. 21:1974-Abstract of Compt. Rend. 184, 751 (1927).
C.A. 21:3042-Abstract of Bull. Soc. Chim. 41,862 (1927).
C.A. 22:1151-Abstract of J. Russ. Phys.-Chem. Soc. 59,537 (1927).
Organic Synthesis, Collective, vol. 2, 167–169, (1943).

*Primary Examiner*—Paul J. Killos

*Attorney, Agent, or Firm*—J. Frederick Thomsen; William P. Heath, Jr.

[57] ABSTRACT

Disclosed are novel 1,5-bis(substituted-aryl)-3-pentanols which are useful in the preparation of polymeric materials and have the formula:

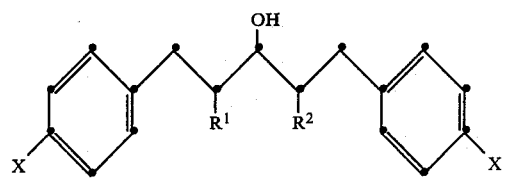

wherein:

$R^1$ and $R^2$ each is hydrogen, alkyl containing up to about 6 carbon atoms or phenyl or collectively $R^1$ and $R^2$ are 1,2- or 1,3-alkylene or 1,2-phenylene; and each X is carboxyl, alkoxycarbonyl of up to about 7 carbon atoms, hydroxyalkoxycarbonyl of up to about 9 carbon atoms, formamido, alkanoylamido having up to about 6 carbon atoms or hydroxyalkoxy having up to about 10 carbon atoms. The novel compounds may be prepared by first condensing certain 4-substituted-benzaldehydes with ketones to obtain intermediate 1,5-bis(4-substituted-aryl)penta-1,4-dien-3-ones and hydrogenating the intermediates with certain catalysts. Mixed copper-chromium oxides are especially effective in converting the pentadienone compounds to the pentanol compounds.

9 Claims, No Drawings

1,5-DIARYL-3-PENTANOL COMPOUNDS AND PROCESSES FOR THE PREPARATION THEREOF

This invention concerns certain novel 1,5-diary-3-pentanols which are useful as monomers in the preparation of polymeric materials. This invention also pertains to certain novel 1,5-diaryl-penta-1,4-dien 3-one precursor compounds and to processes for the preparation of such compounds.

It is known that benzaldehyde and certain substituted benzaldehydes may be condensed with acetone to obtain certain unsubstituted and substituted 1,5-diaryl penta-1,4-dien-3-one compounds, also referred to as dibenzalacetones. Typical procedures are described in Org. Syn., Coll. Vol. II, 167 (1943) and British Patent No. 1,442,133. The preparation of certain unsubstituted and substituted 1,5-diaryl-3-pentanols by the catalytic hydrogenation of the 1,5-diaryl penta-1,4-dien-3-one compounds also is described in the literature. British Patent No. 1,442,133 discloses the hydrogenation of 1,5-bis(3',5'-di-t-butyl-4'-hydroxyphenyl)-penta-1,4-dien-3-one to the corresponding 1,5-bis-(3',5'-di-t-butyl-4'-hydroxyphenyl)-pentanol over 5% palladium on carbon at a pressure of 420 to 580 psig pressure. Ipat'ev and Orlov, [Compt. Rend., 184, 751 (C.A. 21:1974; 1927), Bull. Soc. Chim., 41, 862 (C.A. 21:3042; 1927), J. Russ. Phys. Chem. Soc., 59, 537 (C.A. 22:1151; 1927)] describe the catalytic hydrogenation of 1,5-diphenylpenta-1,4-dien-3-one using nickel catalyst and mention specifically that nickel oxide, at 170°-180° C. and 980-1400 psi hydrogen pressure, gives the ketone, 1,5-diphenyl-3-pentanone. They also state that copper oxide is not an effective catalyst. The hydrogenation of 1,5-diphenyl-penta-1,4-dien-3-one to 1,5-diphenyl-3-pentanol at lower pressure and Raney nickel is diclosed in Compt. Rend., 229, 460, (1949). A similar catalytic hydrogenation using a "skeletal" nickel catalyst at 2100 psi hydrogen pressure is disclosed in J. Organomet. Chem., 153, 181 (1978). According to Chem. Ber., 74B, 1195 (1941), a platinum oxide catalyst gives a 1:1 mixture of 1,5-diphenyl-3-pentanone and 1,5-diphenyl-3-pentanol.

The novel 1,5-bis(substituted-aryl)- 3-pentanols provided by this invention, unlike the known compounds, are useful as monomers, either directly or indirectly, in the manufacture of polymeric materials. These novel compounds have the general formula

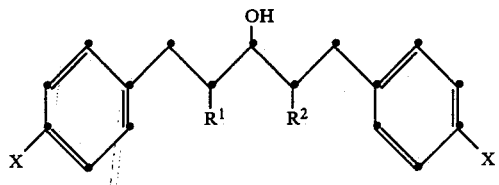

wherein:
$R^1$ and $R^2$ each is hydrogen, alkyl containing up to about 6 carbon atoms or phenyl or collectively $R^1$ and $R^2$ are 1,2- or 1,3-alkylene or 1,2-phenylene; and each X is carboxyl, alkoxycarbonyl of up to about 7 carbon atoms, hydroxyalkoxycarbonyl of up to about 9 carbon atoms, formamido, alkanoylamido having up to about 6 carbon atoms or hydroxyalkoxy having up to about 10 carbon atoms. The above compounds wherein X is an amide group may be converted to diamine compounds according to known procedures and reacted with dicarboxylic acids to produce polyamides. The other compounds encompassed by formula (I) may be used in the preparation of polyesters.

The preferred 1,5-bis(substituted-aryl)-3-pentanols provided by this invention are those wherein $R^1$ and $R^2$ each is hydrogen or methyl or $R^1$ and $R^2$ collectively are 1,3-propanediyl and each X is carboxyl, methoxycarbonyl, ethoxycarbonyl or 2-hydroxyethoxy. These preferred compounds are particularly valuable branching components in the preparation of unsaturated polyesters which, when combined with an arylvinyl compound such as styrene, may be cured to provide resins having unique properties such as excellent solvent resistance.

The novel 1,5-bis(4'-substituted-aryl)-3-pentanols described hereinabove are prepared by the steps comprising:

(1) reacting a 4'-substituted benzaldehyde having the formula

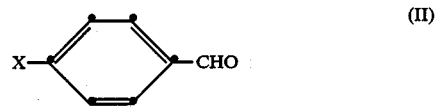

with a ketone having the formula

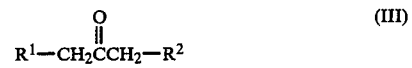

in the presence of an acidic or basic condensation catalyst to obtain a 1,5-bis(4'-substituted-aryl)penta-1,4-dien-3-one intermediate compound having the formula

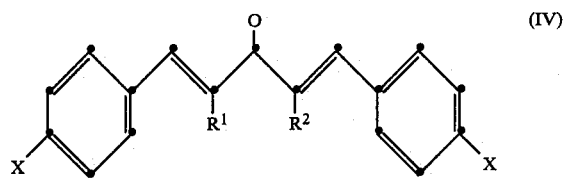

(2) hydrogenating the intermediate compound in the presence of a catalytic amount of a hydrogenation catalyst selected from mixed copper-chromium oxides and supported Group VIII noble metals under hydrogenation conditions of pressure and temperature.

The first step of the above-described process is carried out by reacting approximately 2 moles of the aldehyde per mole of ketone in the presence of an acidic or basic catalyst. Examples of materials which may be used as the catalyst include the alkali metal hydroxides, alkoxides and carbonates; the alkaline earth hydroxides and oxides; quaternary ammonium hydroxides such as tetra-unsubstituted or substituted alkylammonium hydroxides wherein the four alkyl residues contain a total of up to about 20 carbon atoms; alkyl- and aryl-sulfonic acids; acidic ion exchange resins such as Amberlyst 15; and mineral acids such as sulfuric and hydrochloric acid. The condensation reaction normally is conducted in the presence of an inert solvent such as aliphatic and aromatic hydrocarbons, e.g., having from about 6 to 12 carbon atoms and alkanols, e.g., having up to about 6 carbon atoms. The temperature of the condensation step can be varied substantially depending on a number of factors such as the reactants and catalyst being used, catalyst concentration, etc. Although temperatures as low as −25° C. and as high as 300° C. may be used under some circumstances, the condensation reaction normally will be performed at a temperature in the range of about 0° to 140° C. pressure is not normally important and, while pressure moderately above or below atmospheric may be used, the first step most conveniently is done at ambient pressure.

Examples of the Group VIII noble metals which may be used to catalyze the hydrogenation include ruthenium, rhodium, palladium and platinum. Examples of the materials on which the Group VIII noble metals may be supported include silica, alumina, alumina-silica, carbon, titania, etc. The preferred hydrogenation catalysts in terms of both selectivity and yield are mixed copper-chromium oxides, commonly referred to as copper chromite. The concentration of the Group VIII metal or mixed copper-chromium oxide catalyst can vary substantially depending on a number of factors such as the activity and/or selctivity of the particular catalyst, the surface area of the catalyst, the hydrogenation conditions, the mode of operation, etc. For example, when using a trickle-bed hydrogenation system wherein a solution of a 1,5-bis(4'-substituted aryl)penta-1,4-dien-3-one flows over and through one or more fixed beds of the catalyst in granular form in a hydrogen atmosphere at elevated temperature and pressure, the concentration of the catalyst relative to the reactant cannot be determined with any degree of accuracy.

The hydrogenation conditions of temperature and pressure may vary over a wide range depending, for example, on the factors referred to above concerning catalyst concentration. Furthermore, to some extent, temperature and pressure are interdependent and, thus, increasing one may permit lowering of the other. Generally, the hydrogenation conditions will be within the ranges of about 20° to 300° C. and about 50 to 3000 psig hydrogen. The preferred ranges are about 150° to 250° C. and about 500 to 1500 psig hydrogen. Typically, the hydrogenation is carried out in the presence of an inert organic solvent for the 1,5-bis(4'-substituted-aryl)penta-1,4-dien-3-one. Examples of solvents which may be used include hydrocarbons such as aliphatic, cycloaliphatic and aromatic hydrocarbons containing about 6 to 12 carbon atoms, e.g., benzene, toluene, xylene, cumene, psuedocumene, diisopropylbenzene, cyclohexane, hexane, heptane, etc.; carboxylic acid esters such as alkyl carboxylates containing up to about 6 carbon atoms, e.g., methyl acetate, ethyl acetate, methyl butyrate, etc; alkanols containing up to about 6 carbon atoms, e.g., methanol, ethanol, 2-propanol, etc. The concentration of the pentadienone reactant in the solvent is not important and is limited only by the solubility op the particular reactant in the solvent being used and economic considerations. For most reactants the preferred inert organic solvents are toluene, xylene and cyclohexane.

An especially preferred embodiment of our invention comprises a process for the preparation of a 1,5-bis(4-substituted-aryl)-3-pentanol having the formula

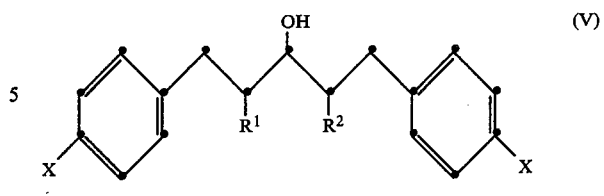

which comprises hydrogenating a 1,5-bis(4'-substituted-aryl)penta-1,4-dien-3-one compound having the formula

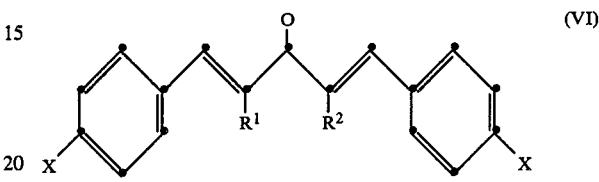

in the presence of a catalytic amount of a mixed copper-chromium oxide catalyst under hydrogenation conditions of pressure and temperature, wherein $R^1$, $R^2$ and X are defined above. The preferred hydrogenation conditions are within the range of about 50° to 300° C. and about 200 to 5000 psig with 150 to 250° C. and 500 to 1500 psig being particularly preferred.

Our invention is further illustrated by the following examples. Examples 1–4 exemplify the preparation of the 1,5-bis(4'-substituted-aryl)-penta-1,4-dien-3-one compounds of formula (IV).

EXAMPLE 1

Acetone (14.5 g, 18.3 mL, 0.25 mol) is added to a solution of methyl 4-formylbenzoate (MFB, 90.3 g, 0.55 mol) prepared and maintained under an inert atmosphere in a 1 L, 3-necked, round-bottom flask equipped with a mechanical stirrer. The flask is placed in a cold water bath and a solution of sodium hydroxide (2.5 g, 0.0625 mol) in 25 mL of equal parts by weight methanol and water is added slowly using an addition funnel. Commencement of reaction is slow, presumably because of acidic impurities in the MFB. The reaction mixture initially turns yellow and as the reaction progresses a light yellow precipitate forms which subsequently becomes a thick slurry. After 2.5 hours the reaction mixture is filtered and the crude product obtained is washed with methanol until the wash solution is no longer a dark color. The product is air dried on the filter to yield 82.9 g (95% of theory) of 1,5-bis(4'-methoxycarbonylphenyl)penta-1,4-dien-3-one, which may be further purified, if desired, by recrystallization from acetic acid or xylene. Analytical results are consistent with the structure expected:

HNMR(CDCL3, 270 MHz): del=3.93 (s,6H), 7.15 (d,2H, J=16 Hz), 7.68 (d,4H, J=10 Hz), 7.76 (d,2H, J=16 Hz), 8.09 (d,4H, J=10 Hz).

IR (KBr): 1720, 1653, 1284 cm(−1).

Elemental analysis: Calc. for $C_{21}H_{18}O_5$: C,71.99; H,5.18. Found: C,71.98; H,5.15.

Melting point: 221°–223° C.

EXAMPLE 2

Example 1 is repeated except that the sodium hydroxide is added while the reaction mixture is maintained at slow reflux (approximately 65° C). The reaction requires twice the quantity of sodium hydroxide as is used in Example 1. The product is isolated and purified as described in Example 1 to give a 76% yield of 1,5-bis(4'-methoxycarbonylphenyl)penta-1,4-dien-3-one.

EXAMPLE 3

To a solution of methyl p formylbenzoate (186.0 g, 1.13 mol) and cyclohexanone (50.4 g, 0.514 mol) in 1 L of methanol, prepared and maintained under an inert atmosphere in a 2 L, 3-necked, round bottom flask equipped with a mechanical stirrer, is added 20 mL of an aqueous solution containing sodium hydroxide (4.0 g, 0.1 mol). The mixture is stirred at ambient temperature for 4.5 hours and the reaction mixture is then filtered and the product dried to give 113.2 g of 2,6-bis(4'-methoxycarbonylbenzylidene)cyclohexanone. The filtrate is heated on a steam bath for 45 minutes, cooled and filtered to give an additional 27.9 g of product for a total yield of 141.1 g (70% of theory) of 2,6-bis(4'-methoxycarbonylbenzylidene)-cyclohexanone. The results from analyses of a sample recrystallized from acetic acid are:

HNMR (CD13, 270 MHz): del=1.82 (quintet, 2H), 2.95 (t,4H), 3.94 (s,6H), 7.52 (d,4H), 7.79 (s,2H), 8.08 (d,4H).

IR ($CH_2Cl_2$) 1272, 1666,1720 cm(−1).

FDMS: M+/e=390.

Elemental analysis: Calc. for $C_{24}H_{22}O_5$: C,73.83; H,5.68. Found: C,73.85; H, -.

Melting point: 203.5°–205.5° C.

EXAMPLE 4

The procedure described in Example 1 is repeated using 4-(2'-hydroxy)ethoxybenzaldehyde in place of MFB and carrying out the reaction for a period of 6 hours to obtain 1,5-bis-[4'-(2''-hydroxy)ethoxyphenyl-penta-1,4-dien-3-one in a 95% yield. Analytical results are consistent with the expected structure:

HNMR (CDC13, 270 MHz): del=3.88 (quart.,4H), 4.11 (t,4H), 4.69 (t,2H), 6.96 (d,4H, J=9 Hz), 7.00 (d,2H, J=16 Hz), 7.66 (d,4H, J=9 Hz), 7.69 (d,2H, J=16 Hz).

IR (KBr): 3100–3600 cm(−1) (s,v. br.), 1650 cm(−1) (s).

FDMS: 354.

Melting point: 169°–170° C.

EXAMPLE 5

An autoclave containing a mixture of 1,5-bis(4'-methoxycarbonylphenyl)penta-1,4-dien-3-one (175.0 g, 0.5 mol), mixed copper-chromium oxide catalyst (17.5 g,) and toluene is pressurized to 250 psi with hydrogen and then heated to 180° C. at which time the total pressure is adjusted to 1000 psi. After maintaining the temperature at 180° C. and the pressure at 1000 psi for 5 hours, the autoclave is cooled and vented. The contents of the autoclave are transferred to and heated in a 2 L Erlenmeyer flask to above 90° C. and filtered using a pad of Celite filter aid (to assist in catalyst removal) in a steam-jacketed Buchner funnel. The filtrate is cooled to room temperature and filtered to give 142.1 g of product, 1,5-bis(4-methoxycarbonylphenyl)-3-pentanol, as a white, fluffy, crystalline material. The volume of the filtrate is reduced 500–600 mL, heated to dissolve the resulting precipitate and cooled to recrystallize the residual product. Filtration of the mixture gives 13.9 g of additional product. A second volume reduction to about 250 mL gives an additional 5.2 g of product. The three crops of crystals are indistinguishable by chromatography and total 161.2 g, 91% of theory.

HNMR (CDC13, 270 MHz): del=1.81 (t,4H), 2.77 (m,4H), 3.88 (s,6H), 7.21 (d,4H), 7.91 (d,4H).

IR (KBr): 1720, 1290 cm( 1); (mull) 3460 (cm 1).

FDMS: M+/e=356.

Elemental analysis: Calc. for $C_{21}H_{24}O_5$: C,70.77; H,6.79. Found: C,71.09; H,6.68.

Melting point: 129°–130° C.

The mixed copper-chromium oxide catalyst employed in this example may be obtained from Harshaw Chemical Company (Cu-1800P) or Aldrich Chemical Company (copper chromite). Three different mixed copper-chromium oxide catalysts, all having the gross stoichiometry $CuO-Cr_2O_3$, did not vary noticeably in performance.

EXAMPLE 6

An autoclave containing 1,5-bis(4'-methoxycarbonylphenyl)penta-1,4-dien-3-one (10.0 g, 0.0286 mol), 5% ruthenium on carbon (1.0 g) and toluene (100 mL) is pressurized to 50 psig with hydrogen, heated to 175° C. and then pressurized to a total pressure of 250 psig with hydrogen. The autoclave is maintained at 175° C. and 250 psig for 6 hours and then cooled and vented. Gas chromatography analysis of the resulting reaction mixture shows that the product mixture consists of 53% 1,5-bis(4'-methoxycarbonyl-phenyl)-3-pentanol and 16% 1,5-bis(4'-methoxycarbonylphenyl)-3-pentanone with the remainder being unidentified compounds.

EXAMPLE 7

An autoclave containing 1,5-bis(4'-methoxycarbonylphenyl)penta-1,4-diene-3-one (5.0 g, 0.0143 mol), 5% rhodium on carbon (0.5 g) and cyclohexane (75 mL) is pressurized to 50 psig with hydrogen, heated to 175° C. and then pressurized with hydrogen to a total pressure of 250 psig. The autoclave is maintained at 175° C. and 250 psig for 6 hours and then cooled and vented. Gas chromatography analysis shows that, after solvent subtraction, the crude product consists of 19% 1,5-bis(4-methoxycarbonyphenyl)-3-pentanol and 75% 1,5-bis(4'-methoxycarbonylphenyl)-3-pentanone with the remainder being other unidentified compounds.

EXAMPLE 8

An autoclave containing 1,5-bis(4'-methoxycarbonylphenyl)penta-1,4-diene-3-one (5.0 g, 0.0143 mol), 0.5% palladium on alumina (0.5 g) and cyclohexane (75 mL) is pressurized to 50 psig with hydrogen, heated to 175° C. and then pressurized with hydrogen to a total pressure of 250 psig. The autoclave is maintained at 175° C. and 250 psig for 6 hours and then cooled and vented. Gas chromatography analysis shows that, after solvent subtraction, the crude product consists of 26% 1,5-bis(4'-methoxycarbonyphenyl)-3-pentanol and 54% 1,5-bis(4'-methoxycarbonylphenyl)-3-pentanone with the remainder being other unidentified compounds.

EXAMPLE 9

An autoclave containing 2,6-bis(4'-methoxycarbonylbenzylidene)cyclohexanone (5.0 g, 0.0128 mol), 5% platinum on carbon (0.5 g) and toluene (100 mL) is pressurized to 50 psig with hydrogen, heated to 175° C. and then pressurized with hydrogen to a total pressure of 250 psig. The autoclave is maintained at 175° C. and 250 psig for 6 hours and then cooled and vented. The contents of the autoclave are transferred to a round bottom flask and the solvent removed. The residue is dissolved in a minimum of methylene chloride and the products separated using medium pressure liquid chromatography to yield 2.73 g (0.0069 mol) of 2,6-bis(4'-methoxycarbonylbenzylidene)cyclohexanone and 1.03 g (0.0026 mol) of 2,6-bis(4'-methoxycarbonylbenzylidene)cyclohexanol. Both the ketone product [FDMS: M+/e=394; IR (CH$_2$Cl$_2$): 1273, 1690, 1720 cm(−1)] and the alkanol product [FDMS: M+/e=396; IR (CH$_2$Cl$_2$): 1284, 1720, 3500 (br) cm(−1)] are obtained as a mixture of the cis and trans cyclohexanol isomers which are identified on the basis of their infrared and mass spectra.

EXAMPLE 10

A mixture of 1,5-bis(4'-methoxycarbonylphenyl)-3-pentanol and 1 L of 3 M aqueous sodium hydroxide are heated at reflux for 7 hours, the resulting reaction mixture is allowed to cool to room temperature and added to a stirred mixture of 300 mL concentrated hydrochloric acid and 200 g of ice. The precipitate is collected by filtration and recrystallized from 3 L of acetic acid. The purified product is dried by heating under vacuum to give 330 g (100% of theory) of 1,5-bis(4'-carboxyphenyl)-3-pentanol as a white, fine, crystalline powder.

HNMR (DMSO, 270 MHz) del=1.67 (m,4H), 2.70 (m,4H), 3.41 (m,1H), 4.43 (d,1H), 7.37 (d,4H), 7.80 (d,4H).

IR (KBr): 2950 (s,v,br.), 1687 cm(−1).
FDMS: M+/e=329 (M+1).
Melting point: 231°-233° C.

EXAMPLE 11

Using essentially the same procedure as described in Example 5, 1,5-bis[4'-(2''-hydroxy)-ethoxyphenyl]-3-pentanol is obtained in a yield of 72% by hydrogenating 1,5-bis[4 (2-hydroxy)ethoxyphenyl]penta-1,4-dien-3-one in the presence of mixed copper-chromium oxide catalyst. The identity of the product is confirmed by analyses:

HNMR(CDCl$_3$, 270MHz): del=1.68 1.82 (m,4H), 1.88 (s,3H), 2.55-2.77 (m,4H), 3.57-3.66 (m,1H), 3.95 (t,4H), 4.06 (t,4H), 6.83 (d,4H), 7.08 (d,4H).

IR (KBr): 3100-3600 cm(−1) (5,v.br.).
FDMS: M+/e=360.
Elemental analysis: Calc: C, 69.98; H, 7.83. Found: C, 70.22; H, 8.01.
Melting point: 103°-104° C.

The invention has been described in detail with particular reference to preferred embodiments thereof, but it will be understood that variations and modifications will be effected within the spirit and scope of the invention.

We claim:
1. A monomer compound having the formula

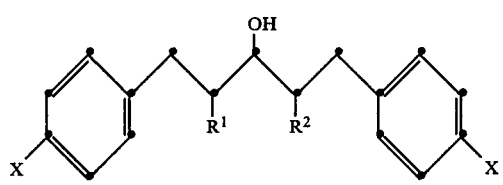

wherein:
R$^1$ and R$^2$ each is hydrogen, alkyl containing up to about 6 carbon atoms or phenyl or collectively R$^1$ and R$^2$ are 1,2- or 1,3-alkylene or 1,2-phenylene; and each X is carboxyl, alkoxycarbonyl of up to about 7 carbon atoms, hydroxyalkoxycarbonyl of up to about 9 carbon atoms, formamido, alkanoylamido having up to about 6 carbon atoms or hydroxyalkoxy having up to about 10 carbon atoms.

2. A monomer compound according to claim 1 wherein R$^1$ and R$^2$ each is hydrogen, methyl or R$^1$ and R$^2$ collectively are 1,3-propanediyl and each X is carboxyl, methoxycarbonyl, ethoxycarbonyl or 2-hydroxyethoxy.

3. A monomer compound according to claim 1 having the formula

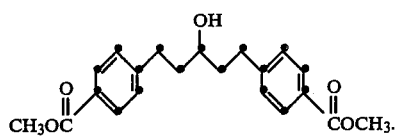

4. A monomer compound according to claim 1 having the formula

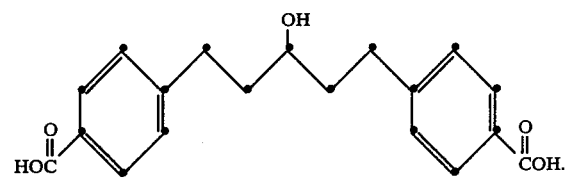

5. A monomer compound according to claim 1 having the formula

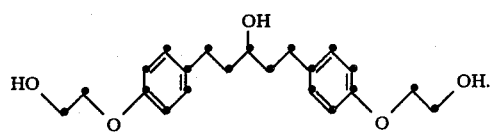

6. Process for the preparation of monomer compounds having the formula:

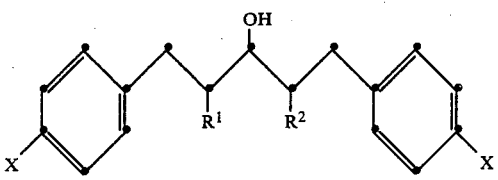

which comprises the steps of
(1) reacting a 4-substituted-benzaldehyde having the formula:

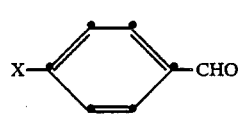

with a ketone having the formula:

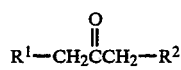

in the presence of an acidic or basic condensation catalyst to obtain an intermediate compound having the formula:

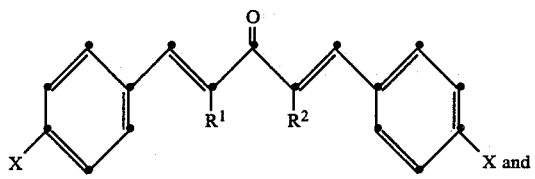

(2) hydrogenating the intermediate compound in the presence of a catalytic amount of a hydrogenation catalyst selected from mixed copper-chromium oxides and supported Group VIII nobel metals under hydrogenation conditions of pressure and temperature; wherein $R^1$ and $R^2$ each is hydrogen, alkyl containing up to about 6 carbon atoms or phenyl or collectively $R^1$ and $R^2$ are 1,2- or 1,3-alkylene or 1,2-phenylene; and each X is carboxyl, alkoxycarbonyl of up to about 7 carbon atoms, hydroxyalkoxycarbonyl of up to about 9 carbon atoms, formamido, alkanoylamido having up to about 6 carbon atoms or hydroxyalkoxy having up to about 10 carbon atoms.

7. Process according to claim 6 wherein step (1) is carried out at a temperature of about 30° to 140° C. and the condensation catalyst is an alkali metal hydroxide, an alkaline earth hydroxide or oxide or quaternary ammonium hydroxide and step (2) is carried out at a pressure of about 50 to 3000 psig and a temperature of about 20° to 300° C.

8. Process for the preparation of a monomer compound having the formula:

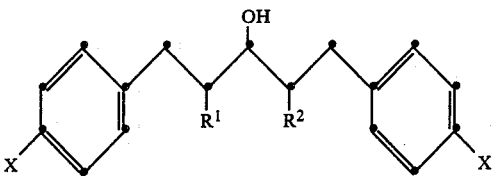

which comprises hydrogenating a compound having the formula:

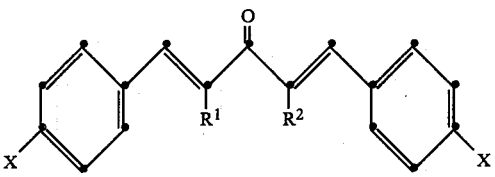

in the presence of a catalytic amount of a mixed copper-chromium oxide catalyst under hydrogenation conditions of pressure and temperature; wherein $R^1$ and $R^2$ each is hydrogen, alkyl containing up to about 6 carbon atoms or phenyl or collectively $R^1$ and $R^2$ are 1,2- or 1,3-alkylene or 1,2-phenylene; and each X is carboxyl, alkoxycarbonyl of up to about 7 carbon atoms, hydroxyalkoxycarbonyl of up to about 9 carbon atoms, formamido, alkanoylamido having up to about 6 carbon atoms or hydroxyalkoxy having up to about 10 carbon atoms.

9. Process according to claim 8 wherein the hydrogenation is carried out at a temperature of about 150° to 250° C. and a pressure of about 500 to 1500 psig.

* * * * *